(12) United States Patent
Iannotti et al.

(10) Patent No.: US 8,763,268 B2
(45) Date of Patent: Jul. 1, 2014

(54) METHOD AND APPARATUS FOR GUIDING MOTION ALONG A DESIRED MOTION TRAJECTORY

(75) Inventors: Joseph P. Iannotti, Strongsville, OH (US); Jason A. Bryan, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 210 days.

(21) Appl. No.: 13/484,335

(22) Filed: May 31, 2012

(65) Prior Publication Data

US 2012/0308322 A1 Dec. 6, 2012

Related U.S. Application Data

(60) Provisional application No. 61/492,639, filed on Jun. 2, 2011.

(51) Int. Cl.
*B23Q 17/22* (2006.01)

(52) U.S. Cl.
CPC .................... *B23Q 17/2266* (2013.01)
USPC ............................ 33/638; 33/645; 408/115 R

(58) Field of Classification Search
CPC ........... B23Q 17/2233; B23Q 17/2266; B23Q 17/2283; B23Q 17/2291; B23B 47/28
USPC ........... 33/613, 628, 632, 636, 638, 639, 645; 408/115 R
See application file for complete search history.

(56) References Cited

U.S. PATENT DOCUMENTS

| | | | | |
|---|---|---|---|---|
| 2,483,060 A | * | 9/1949 | Niedelman et al. | 33/638 |
| 3,707,043 A | * | 12/1972 | Jones | 33/642 |
| 5,465,492 A | * | 11/1995 | Bond | 33/638 |
| 6,214,014 B1 | | 4/2001 | McGann | |
| 6,743,235 B2 | | 6/2004 | Subba Rao | |
| 7,828,806 B2 | | 11/2010 | Graf et al. | |
| 7,946,049 B1 | * | 5/2011 | Wilton | 33/613 |
| 8,343,195 B2 | * | 1/2013 | Rathbun et al. | 606/281 |
| 2004/0215395 A1 | * | 10/2004 | Strasser et al. | 702/9 |
| 2006/0161167 A1 | | 7/2006 | Myers et al. | |
| 2011/0190775 A1 | | 8/2011 | Ure | |
| 2011/0213371 A1 | * | 9/2011 | Anthony et al. | 606/85 |
| 2011/0255928 A1 | * | 10/2011 | Ferreras | 408/115 R |
| 2014/0003875 A1 | * | 1/2014 | SAITO et al. | 408/115 R |

* cited by examiner

*Primary Examiner* — G. Bradley Bennett
(74) *Attorney, Agent, or Firm* — Tarolli, Sundheim, Covell & Tummino LLP

(57) ABSTRACT

A method of longitudinally guiding a first elongate structure for motion along a desired motion trajectory toward a target area through reference to a second elongate structure includes a guiding frame having at least one laterally offset guiding structure. The guiding frame is selectively affixed to the first elongate structure in a predetermined relative guiding configuration. The second elongate structure is placed in a predetermined targeting relationship, correlated with the desired motion trajectory, with the target area. The second elongate structure is maintained in the predetermined targeting relationship substantially lateral to the target area. The second elongate structure is brought into a predetermined guiding relationship with the guiding portion of the guiding frame. A transitory position of the first elongate structure is laterally adjusted during motion toward the target area to maintain the second elongate structure in the predetermined guiding relationship with the guiding portion of the guiding frame.

32 Claims, 4 Drawing Sheets

METHOD AND APPARATUS FOR GUIDING MOTION ALONG A DESIRED MOTION TRAJECTORY

RELATED APPLICATION

This application claims priority from U.S. Provisional Application No. 61/492,639, filed 2 Jun. 2011, the subject matter of which is incorporated herein by reference in its entirety.

TECHNICAL FIELD

The present invention relates to a method and apparatus for guiding motion along a desired motion trajectory and, more particularly, to a method of, and apparatus for, longitudinally guiding a first elongate structure for motion along a desired motion trajectory toward a target area through reference to a second elongate structure.

BACKGROUND OF THE INVENTION

During a surgical procedure, it can be difficult to maintain a steady frame of reference with respect to the patient tissue within the surgical site. For example, the surgery may modify the patient tissue, the patient tissue may move within the patient's body, blood may obscure the patient tissue, local anatomic conditions may require that the patient tissue may be viewed or manipulated at an awkward angle for the surgeon, or the like. In addition, the patient tissue may be slippery or unstable within the surgical site.

Accordingly, a guide pin or guidewire may be temporarily engaged with the patient tissue and protrude therefrom to provide a landmark to orient the user during the surgical procedure. Particularly when the patient tissue of concern is bony or otherwise able to firmly engage and support a rigid structure, an orthopedic guidewire may be attached to the patient tissue to provide a location orientation relative to the patient tissue.

Additionally, a sufficiently sturdy or rigid guidewire may be used as a primary indexing device to physically guide a tool or prosthetic component to a desired location on the patient tissue, and optionally at a desired trajectory. For example, a reamer could have a center hole (i.e., be a "cannulated" tool) that fits over the rigid guidewire for reaming an area of the patient tissue concentrically surrounding the guidewire at a desired location and trajectory. Similarly, an acetabular impactor could be cannulated to fit over the rigid guidewire for impacting a prosthetic acetabular component into place at a desired location and trajectory.

However, it is possible that the "rigid" guidewire may not be sufficiently rigid to hold a tool or prosthetic component as steady as desired to accurately achieve the desired location and/or trajectory of contact with the patient tissue. It is also possible that the rigid guidewire, a guide pin, or another primary or supplemental indexing device might not be able to be placed directly on, in, or at the desired target patient tissue site because that placement will conflict with other operations that are to be performed in the same, possibly spatially constrained, area.

SUMMARY OF THE INVENTION

In an embodiment of the present invention, a method of longitudinally guiding a first elongate structure for motion along a desired motion trajectory toward a target area through reference to a second elongate structure is described. The first elongate structure, including longitudinally spaced proximal and distal first structure ends, is provided. The second elongate structure, including longitudinally spaced proximal and distal second structure ends separated by a second structure body, is provided. A guiding frame having a mounting portion and at least one laterally offset guiding structure is provided. The guiding frame is selectively affixed to the first elongate structure in a predetermined relative guiding configuration. The second elongate structure is placed in a predetermined targeting relationship with the target area. The predetermined targeting relationship is correlated with the desired motion trajectory. The second elongate structure is maintained in the predetermined targeting relationship substantially lateral to the target area with the distal second structure end being located closer to the target area than is the proximal second structure end. At least one of the proximal second structure end and the second structure body is brought into a predetermined guiding relationship with the guiding portion of the guiding frame. The first elongate structure is moved longitudinally toward the target area. A transitory position of the first elongate structure is laterally adjusted during the step of moving the first elongate structure longitudinally toward the target area to maintain the at least one of the proximal second structure end and the second structure body in the predetermined guiding relationship with the guiding portion of the guiding frame.

In an embodiment of the present invention, an apparatus for longitudinally guiding a first elongate structure for motion along a desired trajectory toward a target area through reference to a second elongate structure is described. The first elongate structure includes longitudinally spaced proximal and distal first structure ends. The second elongate structure includes longitudinally spaced proximal and distal second structure ends separated by a second structure body. The second elongate structure is configured for placement in a predetermined targeting relationship with the target area. The predetermined targeting relationship is correlated with the desired motion trajectory. The predetermined targeting relationship includes the second elongate structure being located substantially lateral to the target area with the distal second structure end being located closer to the target area than is the proximal second structure end. A guiding frame has a mounting portion and at least one laterally offset guiding structure. The guiding frame is configured for selective affixation to the first elongate structure in a predetermined relative guiding configuration. At least one of the proximal second structure end and the second structure body is configured for placement into a predetermined guiding relationship with the guiding portion of the guiding frame. The first elongate structure is configured for movement longitudinally toward the target area while a transitory position of the first elongate structure is laterally adjusted to maintain the at least one of the proximal second structure end and the second structure body in the predetermined guiding relationship with the guiding portion of the guiding frame.

In an embodiment of the present invention, a guiding apparatus for longitudinally guiding at least a chosen one of a tool and a prosthetic component along a desired motion trajectory toward a target patient tissue through reference to a guide pin is described. A guiding frame has a mounting portion and at least one laterally offset guiding structure. The guiding frame is configured for selective affixation to the chosen one of the tool and the prosthetic component in a predetermined relative guiding configuration. The guiding portion is configured for placement into a predetermined guiding relationship with at least a portion of the guide pin. The guide pin is configured for placement in a predetermined targeting relationship with the target patient tissue. The predetermined targeting relationship is correlated with the desired motion trajectory. The guide pin is substantially located lateral to the target patient tissue. The chosen one of the tool and the prosthetic component, when in the predetermined relative guiding configuration with the guiding frame, is configured for movement longitudinally toward the target patient tissue while a transitory position of the chosen one of the tool and the prosthetic component is laterally adjusted to maintain the guide pin in the predetermined guiding relationship with the guiding portion of the guiding frame.

BRIEF DESCRIPTION OF THE DRAWINGS

For a better understanding of the invention, reference may be made to the accompanying drawings, in which.

DESCRIPTION OF EMBODIMENTS

Figure 1:
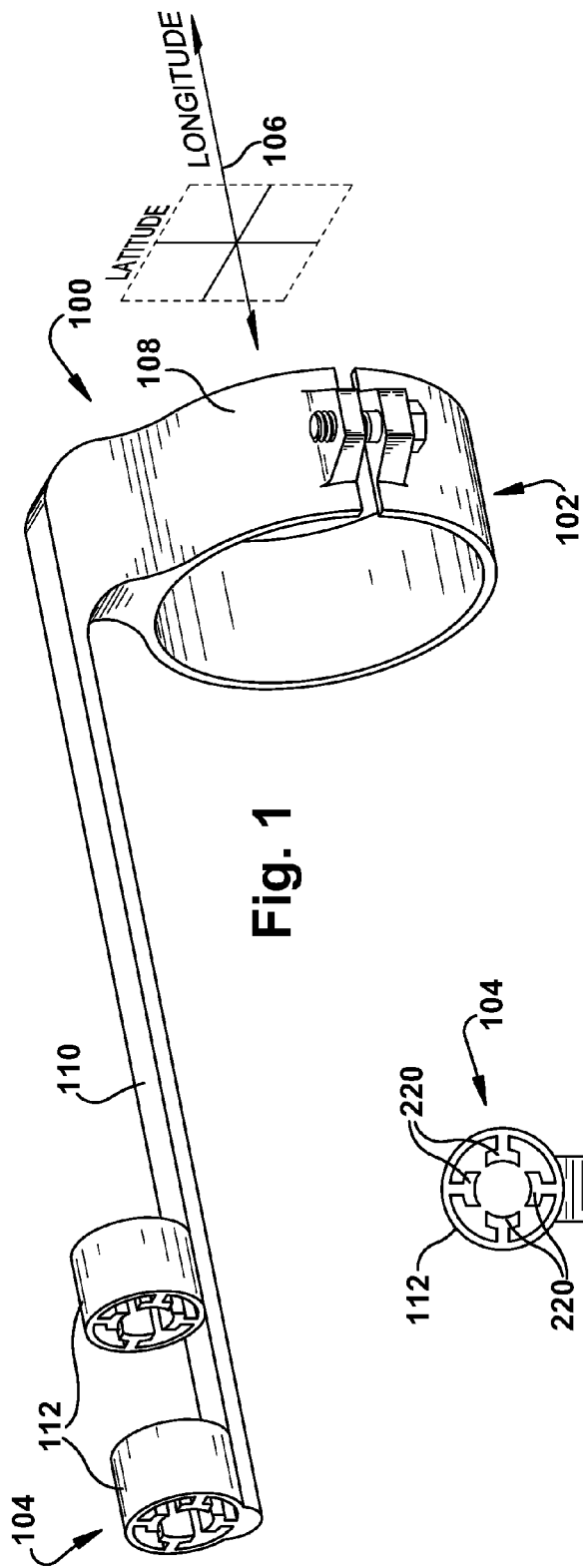
FIG. 1 is a side view of an embodiment of the present invention.

In accordance with the present invention, FIG. 1 depicts a component of an apparatus for longitudinally guiding the motion of a first structure with reference to a second structure. A guiding frame 100 is depicted in FIG. 1. The guiding frame 100 has a mounting portion 102 and at least one laterally offset guiding structure 104. The guiding frame 100 is substantially longitudinally oriented. The longitudinal direction is horizontal, in the orientation of FIG. 1, and a "lateral" direction is substantially perpendicular to the longitudinal direction, as shown via the orientation arrow 106 in FIG. 1.

In the embodiment of the guiding frame 100 shown in FIG. 1, the mounting portion 102 includes a mounting collar 108 that substantially laterally surrounds at least a portion of the first structure to achieve a predetermined relative guiding configuration, as will be discussed below. The mounting collar 108 shown in FIG. 1 is laterally attached to a spacer rod 110 that is, in turn, laterally attached to a guiding portion 104 that includes one or more arcuate guiding sleeves 112 (two shown). It is contemplated, however, that the mounting portion 102 may be directly connected to one or more guiding portions 104 (i.e., omitting the spacer rod 112 or any other intermediate structures) to form the laterally offset relationship between the mounting portion and the guiding portion.

Figure 2:
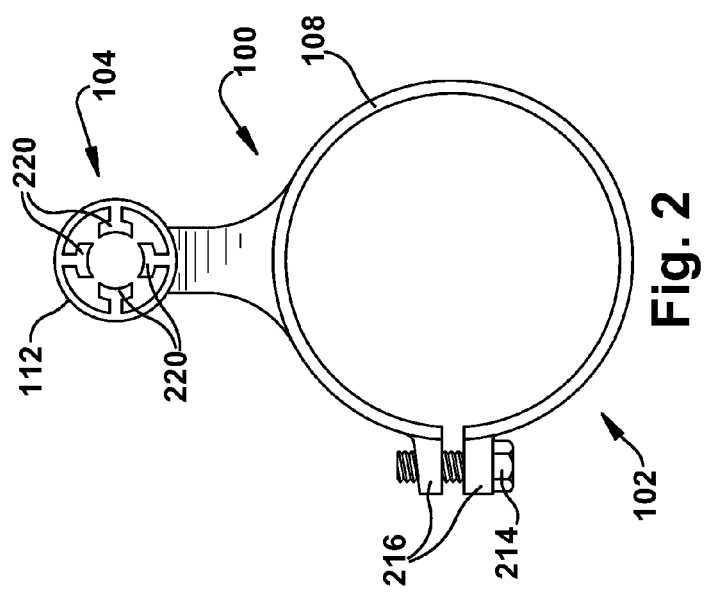
FIG. 2 is a rear view of the embodiment of FIG. 1.

FIG. 2 shows a rear view of the guiding frame 100 shown in FIG. 1. In FIG. 2, the lateral direction is within the plane of the page, and the longitudinal direction is into and out of the page. Each guiding sleeve 112, when present with the guiding portion 104, may substantially laterally surround at least a portion of the second structure to achieve a predetermined relative guiding relationship, as will be discussed below. For example, and as shown in FIG. 2, the guiding sleeve 112 could have a closed circular cross-section and any desired lateral or longitudinal dimensions. It is also contemplated that the guiding portion 104 may include one or more guiding sleeves 112, of any suitable length, having open or closed cross-sectional shapes including, but not limited to, linear, circular, curvilinear, or any combination thereof. The guiding portion 104 could also be a flat surface, a "point" or "tip" of a lateral protrusion away from the mounting collar 108, and may be as rigid or flexible as desired for a particular application of the present invention.

The mounting collar 108 shown in FIG. 2 includes a clamping fastener 214 which selectively interacts with collar ears 216 to slightly reduce and/or expand a diameter of the mounting collar. The clamping fastener 214, or any other reduction/expansion means, can be manipulated by the user in a known manner to "loosen" the mounting collar 108 for placement around the first structure, and then can again be manipulated by the user to "tighten" the mounting collar for frictional and/or clamping engagement with the first structure. In many applications of the present invention, it is desirable for the guiding frame 100 to be substantially relatively stationary with respect to the first structure when the two are affixed together in the predetermined relative guiding configuration.

Figures 3A, 3B, 3C:
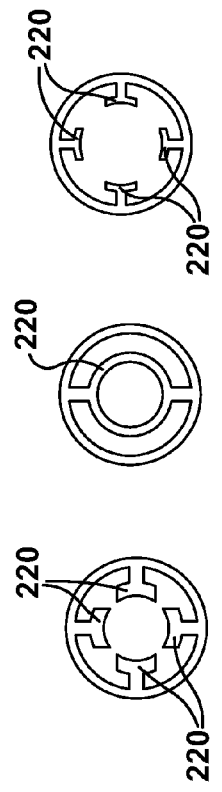
FIGS. 3A-3C depict alternate configurations of a structure of the embodiment of FIG. 1.

As can be seen in FIG. 2, the guiding sleeve(s) 112 include one or more fine-resolution guiding aids 220 to help the user in manually placing the second structure into a desired predetermined guiding relationship with the guiding portion 104 of the guiding frame 100. As an example, that predetermined guiding relationship may be one in which the second structure is substantially laterally centered within a guiding sleeve 112. FIGS. 3A-3C illustrate various configurations of fine-resolution guiding aids 220 for use with the present invention. FIG. 3A includes four fine-resolution guiding aids 220 having "T"-shaped lateral cross-sections that extend inward from the guiding sleeve 112. FIG. 3B includes one fine-resolution guiding aid 220 having a closed circular lateral cross-section that is held or "suspended" within the guiding sleeve 112 by connecting structures. FIG. 3C, like FIG. 3B, includes four fine-resolution guiding aids 220 having "T"-shaped lateral cross-sections, but those in FIG. 3C are smaller (thus giving "coarser" resolution) than those in FIG. 3B. Another contemplated fine-resolution guiding aid 220 arrangement (not shown) includes one or more set screws with a manipulable head located on an outer surface of the guiding sleeve 112 and a shaft extending laterally through the guiding sleeve 112 and into a center portion thereof, such that a user can fine-tune the amount of the set screws that protrudes into the center portion of the guiding sleeve 112 and thereby personalize the guiding function of the fine-resolution guiding aids 220. Any of the fine-resolution guiding aids 220 depicted in the Figures, or any other suitable fine-resolution guiding aids, could be readily provided by one of ordinary skill in the art for a particular application of the present invention as desired. It is also contemplated that the guiding sleeve(s) 112, fine-resolution guiding aid(s) 220, and/or any other structure of the guiding portion 104 may contact the second structure as desired during guiding of the motion of the first structure, but contact between the second structure and any part of the guiding frame 100 is optional in the present invention.

Figure 4:
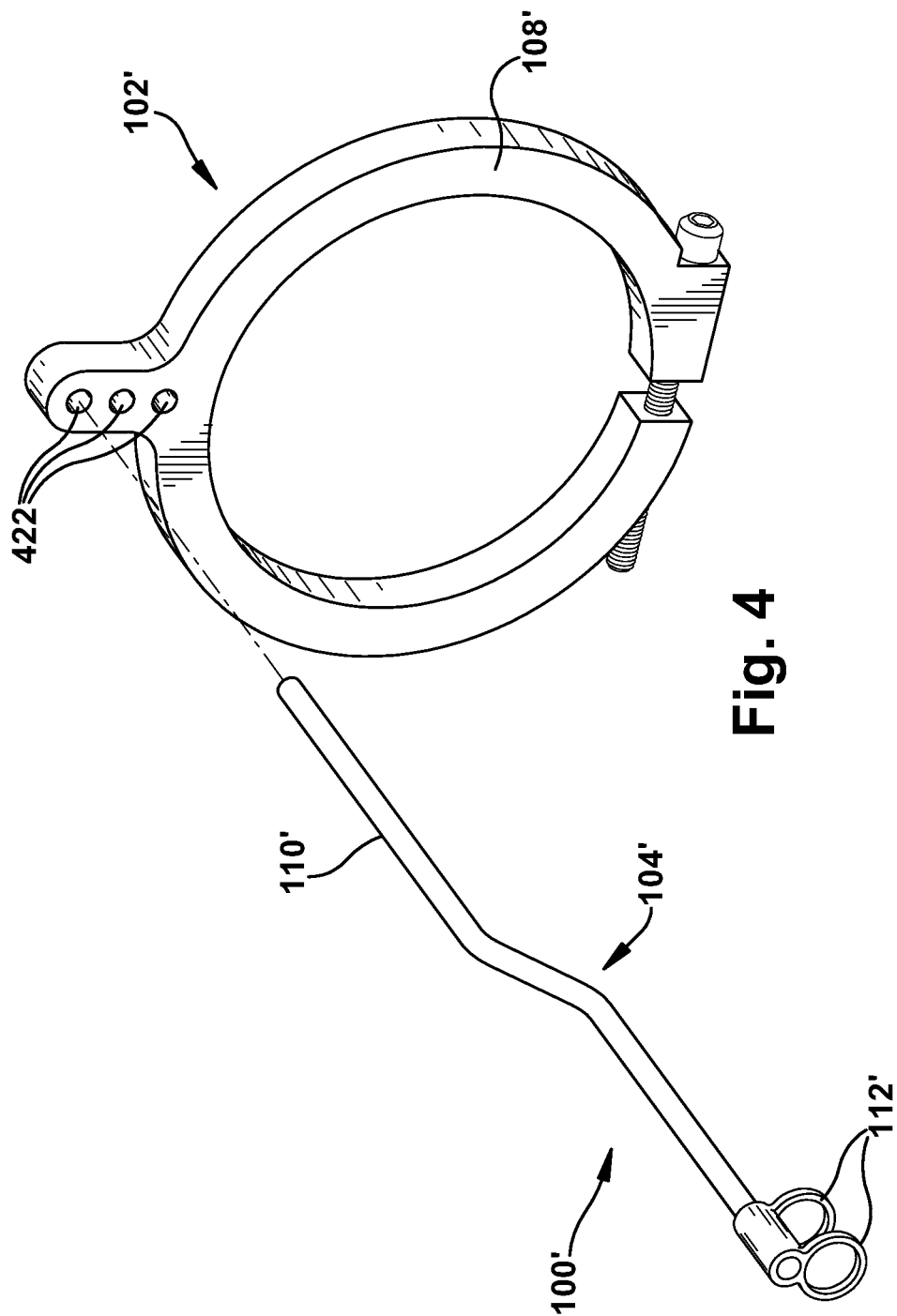
FIG. 4 is an exploded view of an embodiment of the present invention.

FIG. 4 illustrates a second embodiment of a guiding frame 100'. The guiding frame 100' of FIG. 4 is similar to the guiding frame 100 of FIGS. 1-3C and therefore, structures of FIG. 4 that are the same as or similar to those described with reference to FIGS. 1-3C have the same reference numbers with the addition of a "prime" mark. Description of common elements and operation similar to those in the previously described embodiments will not be repeated with respect to the second embodiment.

The guiding frame 100' is shown in exploded view in FIG. 4 to illustrate the manner in which the spacer rod 110' and attached guiding sleeves 112' are optionally removable from the mounting portion 102' of the guiding frame. The guiding frame 100' includes a plurality of laterally offset guiding structures 422 (shown here as being associated with the mounting portion 102'), each of which is configured to receive the spacer rod 110' or another structure of the guiding portion 104' to provide a different lateral position of the guiding portion 104' with respect to the mounting portion 102'. For example, if the user wishes to have the guiding portion 104' at a relatively large lateral offset from the mounting portion 102', the spacer rod 110' could be associated with the topmost laterally offset guiding structure 422 (in the orientation of FIG. 4), whereas associating the spacer rod with the bottom-most laterally offset guiding structure 422 would result in a guiding portion that is at a relatively small lateral offset from the mounting portion.

As may also be seen in FIG. 4, the spacer rod 110' can include a laterally offset or "stepped" portion along a longitudinal length thereof, to further adjust the lateral position of a structure of the guiding portion 104' (e.g., the guiding sleeves 112') with respect to the mounting portion 102'. Multiple stepped spacing rods 110', having different lateral offsets, could be provided to the user. By choosing a desired straight or stepped spacing rod 110', optionally rotating the spacing rod to place any associated guiding sleeve(s) 112' into a desired orientation with respect to the mounting portion 102', and associating that chosen and oriented spacing rod with a desired laterally offset guiding structure 422, the user can place the guiding portion 104' into a desired lateral position with respect to the mounting portion within a fairly wide range of potential lateral positions. Accordingly, the guidance of the first structure with reference to the second structure may be accomplished with a relatively high degree of precision.

Figure 5:
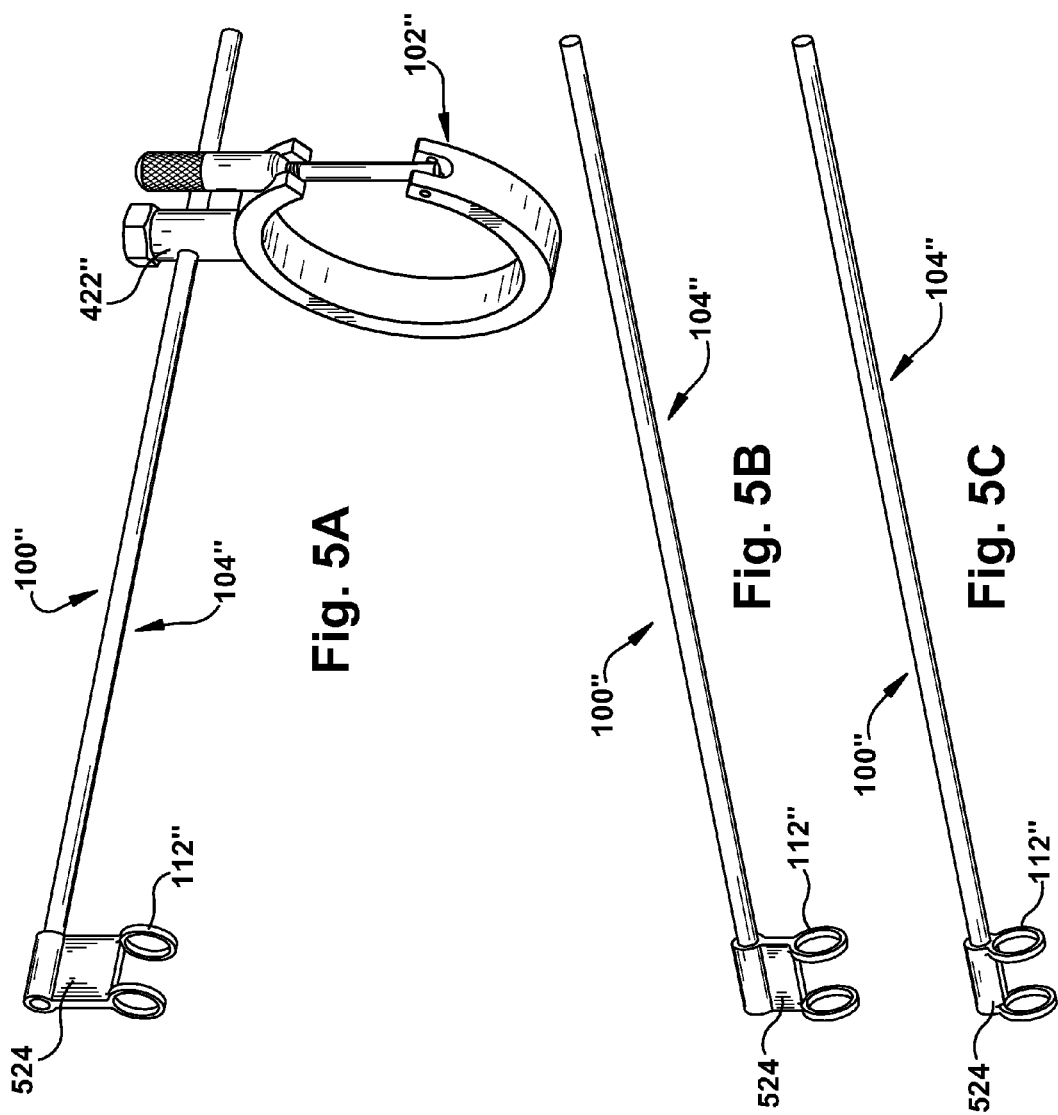
FIGS. 5A-5C are side views of an embodiment of the present invention including alternate configurations.

FIGS. 5A-5C illustrate a third embodiment of a guiding frame 100". The guiding frame 100" of FIGS. 5A-5C is similar to the guiding frame 100 of FIGS. 1-3C and therefore, structures of FIG. 5A-5C that are the same as or similar to those described with reference to FIGS. 1-3C have the same reference numbers with the addition of a double "prime" mark. Description of common elements and operation similar to those in the previously described embodiments will not be repeated with respect to the third embodiment.

The third embodiment of the guiding frame 100" is similar to the second embodiment of the guiding frame 100' in that the laterally offset position of the guiding portion 104" with respect to the mounting portion 102" can be accomplished through selection of a guiding portion. In the third embodiment of the guiding frame 100", a holdoff spacer 524 is used to connect the guiding sleeve 112" to the spacer rod 110". When an array of spacer rods 110"—such as those shown in FIGS. 5A-5C—are provided, each having different sized holdoff spacers 524, the lateral offset of the guiding portion 104" with respect to the mounting portion 102" can be adjusted by the user via selection of a desired spacer rod 110". Through use of a holdoff spacer 524 or similar structure, straight spacer rods 110" can be used as an alternative to the stepped spacer rod 110' shown in FIG. 4, both types of spacer rods facilitating a lateral offset between the guiding portion (e.g., the guiding sleeve[s] 112") and the mounting portion 102".

Figure 6:
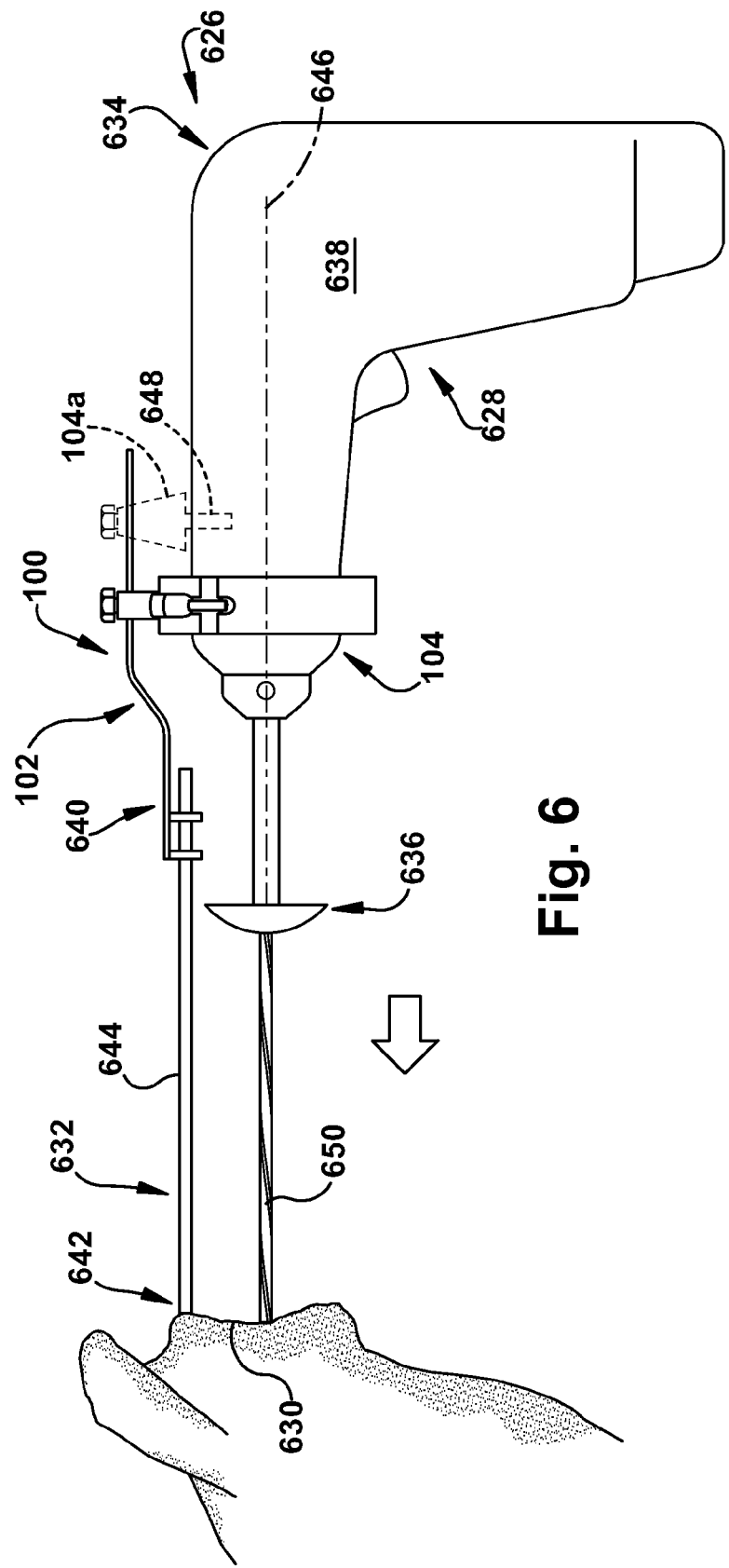
FIG. 6 is a side view of the embodiment of FIG. 4 in an example use environment.

FIG. 6 shows an apparatus 626 for longitudinally guiding a first elongate structure 628 along a desired trajectory toward a target area 630 through reference to a second elongate structure 632. As shown here, the first elongate structure 628 is a surgical drill or other penetration tool, the target area 630 is a patient tissue, and the second elongate structure 632 is a guide pin, but these characterizations and descriptions are not limiting of the nature(s) or use environment(s) of any aspect of the present invention.

The first elongate structure 628 has longitudinally spaced proximal and distal first structure ends 634 and 636, respectively, separated by a first structure body 638. The second elongate structure 632 has longitudinally spaced proximal and distal second structure ends 640 and 642, respectively, separated by a second structure body 644.

The second elongate structure 632 is configured for placement in a predetermined targeting relationship with the target area 630. For example, the distal second structure end 642 could be placed into contact with, or even inserted into, the material of the target area 630 during placement in the predetermined targeting relationship. The predetermined targeting relationship may be correlated with a desired motion trajectory (shown generally by 646) of the first elongate structure 628, which may be a predetermined direct correlation. For example, the second elongate structure 632, whether linear or a more complex shape, could be three-dimensionally oriented with respect to the target area 630 to substantially faithfully replicate the three-dimensional orientation and path of the desired motion trajectory 646 in a slightly offset position from the desired motion trajectory. The predetermined targeting relationship between the second elongate structure 632 and the target area 630 therefore may include the second elongate structure being located substantially lateral to the target area (if not within or at the target area) with the distal second structure end 642 being located longitudinally closer to the target area than is the proximal second structure end 640.

The guiding frame 100 is configured for selective affixation to the first elongate structure 628 in a predetermined relative guiding configuration. Though the example guiding frame 100 of FIG. 6 is similar to that of the second embodiment shown in FIG. 4, any embodiment of the guiding frame, whether or not discussed specifically herein, may be used without harm to the present invention. The guiding frame 100 may be affixed to the first elongate structure 628 in any desired manner. As a first example, the solid-line mounting portion 102 of FIG. 6 is of the mounting collar 108 type (discussed previously with reference to FIG. 1), that substantially laterally surrounds at least a portion of the first elongate structure 628 to achieve the predetermined guiding configuration, and that may be used with a stock or standard first elongate structure that has not been modified for use with the present invention.

An optional dotted-line mounting portion 102a is shown in FIG. 6 as a second example affixation, though it is contemplated that normally only one mounting portion (102, 102a, or another type) would be used at one time. The dotted-line mounting portion 102a is received by a mounting bracket 648 (here, a simple aperture or cavity) of the first elongate structure 638 to achieve the predetermined relative guiding configuration between the guiding frame 100 and the first elongate structure in a way that uses a modified or non-standard first elongate structure that is specialized for use with the guiding frame 100. It is contemplated that a first elongate structure 638 which has this type of direct-mount could also embody a mounting portion 102a which receives a guiding portion 104 directly, in which case the first elongate structure 638 would also comprise a portion of the guiding frame 100.

When a plurality of laterally offset guiding structures 422 are present (as in the second embodiment of FIG. 2), a chosen one of the laterally offset guiding structures may be selected to form the predetermined guiding relationship between the second elongate structure 632 and the guiding frame 100 responsive to a desired lateral offset distance between the second elongate structure and the first elongate structure 628.

Regardless of the manner in which the guiding frame 100 is affixed to the first elongate structure 628, the guiding frame may assist in longitudinally guiding the first elongate structure for motion along the desired motion trajectory 646 toward the target area 630 through reference to the second elongate structure 632. At least one of the proximal second structure end 640 and the second structure body 644 may be configured for placement into a predetermined guiding relationship with the guiding portion 104 of the guiding frame 100. In the configuration of the present invention depicted in FIG. 6, the guiding portion 104 is passed longitudinally over the proximal second structure end 640 and is at least partially laterally surrounding the second structure body 644.

The first elongate structure 628 may be moved longitudinally toward the target area 630 (toward the left, in the configuration of FIG. 6) while a transitory position of the first elongate structure is laterally adjusted to maintain the predetermined guiding relationship between the guiding portion 104 and at least a portion of the second elongate structure 632. In other words, as the user moves the first elongate structure 628 toward the target area 630, the user can observe the relative positioning of the second elongate structure 632 (a guide pin, as shown in FIG. 6) with respect to the guiding portion 104. With the assistance of the guiding frame 100, the user can make realtime adjustments to the lateral position of the first elongate structure 628 to keep the first elongate structure at a desired lateral offset from the second elongate structure 632. Because the second elongate structure 632 is configured and/or positioned to echo or embody the desired motion trajectory 646 and because at least a portion of the guiding frame 100 is in a known and (for many embodiments of the present invention) constant relative guiding configuration with respect to the first elongate structure 628, the user can move the first elongate structure longitudinally substantially along the desired motion trajectory with the assistance of the lateral adjustments made to maintain at least a portion of the second elongate structure 632 in the predetermined guiding relationship with at least a portion of the guiding frame 100. Optionally, the transitory position of the first elongate structure 628 may be laterally adjusted during longitudinal motion of the first elongate structure to substantially maintain the predetermined guiding relationship using at least one fine-resolution guiding aid 220 of the guiding portion 104 of the guiding frame 100.

As shown in FIG. 6, the guiding portion 104 may be located lateral to the first structure body 638 such that the distal first structure end 636 is located longitudinally closer to the target area 630 than is the guiding portion 104 while the first elongate structure 638 is being moved longitudinally toward the target area, such that the distal first structure end contacts the target area before the guiding portion and/or any other portion of the guiding frame 100 does (if the guiding portion and/or guiding frame indeed ever comes into contact with the target area).

This property of the present invention may be of interest, for example, as in the situation shown in FIG. 6, where a tool and/or a prosthetic component (here, a surgical drill) serves as the first elongate structure 638. The FIG. 6 arrangement includes a handle end as the proximal first structure end 634 and a tissue-contacting end (such as the depicted cannulated drill bit) as the distal first structure end 636. An optional second guide pin 650 is shown in FIG. 6 as selectively engaging with the cannulated drill bit comprising the distal first structure end 634 to assist with keeping motion of the first elongate structure substantially along a trajectory substantially parallel to—or superimposed upon—the desired motion trajectory 646. If some structure of the guiding frame 100 were to come into contact with the target area 630 or a neighbouring structure before the drill bit—serving as the distal first structure end 634—contacts the target area, interference between the target area and the guiding frame may prevent the drill bit from reaching and/or penetrating the target area in the desired manner. It is contemplated that the guiding frame 100 or some portion thereof may be slidable, collapsible, telescoping, or otherwise configured to longitudinally shorten at a predetermined time during use of the apparatus 100, if desired to permit contact between the distal first structure end 634 and the target area 630, however. It is also contemplated that the guiding frame 100 could be positioned and/or configured with respect to the first elongate structure 628 to place the guiding portion 104 toward, or even longitudinally beyond, the proximal first structure end 634.

It is contemplated that any suitable means, or combination thereof, may be provided to assist the user by detecting and/or giving feedback on the predetermined guiding relationship between the guiding portion 104 and at least a portion of the second elongate structure 632. For example, vibrations, lights, and/or sounds could indicate to the user the status of the predetermined guiding relationship (i.e., whether the guiding portion 104 is "on" or "off" target with the second elongate structure 632); magnetic, acoustic, laser, sonar, camera, or other noncontact proximity/alignment detection means could be provided; or any other assistive technologies could be provided to assist the user with achieving and maintaining the predetermined guiding relationship between the guiding portion 104 and at least a portion of the second elongate structure 632.

When the first elongate structure 628 has sufficiently advanced longitudinally toward the target area 630, along the desired motion trajectory 646, the distal first structure end 636 may approach the target area 630. As desired, the distal first structure end 636 may come into contact with the target area 630. In certain applications of the present invention, the distal first structure end 636 may selectively penetrate the target area 630 (for example, if the distal first structure end includes a drill bit or other cutting edge) along the desired motion trajectory 646 by continued longitudinal guidance using the guiding frame 100 after the distal first structure end has initially contacted the target area.

While aspects of the present invention have been particularly shown and described with reference to the preferred embodiment above, it will be understood by those of ordinary skill in the art that various additional embodiments may be contemplated without departing from the spirit and scope of the present invention. For example, any of the described structures and components could be integrally formed as a single piece or made up of separate sub-components, with either of these formations involving any suitable stock or bespoke components and/or any suitable material or combinations of materials. It is contemplated that at least a portion of the apparatus may be reusable (optionally sterilizable) or disposable, as desired for a particular application of the present invention. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A variety of schemes are described herein for placing the apparatus into the predetermined position with respect to the patient tissue, and these schemes can be used singly or in any suitable combination for a particular application of the present invention. The apparatus, or portions thereof, could be anchored to the patient tissue in any suitable manner, such as, but not limited to, adhesives, integral pegs, other fasteners, frictional engagement, magnets, any other suitable mounting feature types, or any combination thereof. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A method of longitudinally guiding a first elongate structure for motion along a desired motion trajectory toward a target area through reference to a second elongate structure, the method comprising the steps of:
   providing the first elongate structure, including longitudinally spaced proximal and distal first structure ends;
   providing the second elongate structure, including longitudinally spaced proximal and distal second structure ends separated by a second structure body;
   providing a guiding frame having a mounting portion and at least one laterally offset guiding structure;
   selectively affixing the guiding frame to the first elongate structure in a predetermined relative guiding configuration;
   placing the second elongate structure in a predetermined targeting relationship with the target area, the predetermined targeting relationship being correlated with the desired motion trajectory;
   maintaining the second elongate structure in the predetermined targeting relationship substantially lateral to the target area with the distal second structure end being located closer to the target area than is the proximal second structure end;
   bringing at least one of the proximal second structure end and the second structure body into a predetermined guiding relationship with the guiding portion of the guiding frame;
   moving the first elongate structure longitudinally toward the target area; and
   laterally adjusting a transitory position of the first elongate structure during the step of moving the first elongate structure longitudinally toward the target area to maintain the at least one of the proximal second structure end and the second structure body in the predetermined guiding relationship with the guiding portion of the guiding frame.

2. The method of claim 1, wherein the step of laterally adjusting a transitory position of the first elongate structure during the step of moving the first elongate structure longitudinally toward the target area results in movement of at least a portion of the first elongate structure moving substantially along the desired motion trajectory.

3. The method of claim 1, wherein the predetermined targeting relationship bears a predetermined direct correlation with the desired motion trajectory.

4. The method of claim 1, wherein the step of placing the second elongate structure in a predetermined targeting relationship with the target area includes the step of contacting the target area with the distal second structure end.

5. The method of claim 1, wherein the proximal and distal first structure ends are longitudinally separated by a first structure body, and the guiding portion is located lateral to the first structure body such that the distal first structure end is located longitudinally closer to the target area than is the guiding portion during the step of moving the first elongate structure longitudinally toward the target area.

6. The method of claim 5, wherein the distal first structure end selectively penetrates the target area along the desired trajectory.

7. The method of claim 1, wherein the mounting portion of the guiding frame includes a mounting collar that substantially laterally surrounds at least a portion of the first elongate structure to achieve the predetermined relative guiding configuration.

8. The method of claim 1, wherein the mounting portion of the guiding frame is received by a mounting bracket of the first elongate structure to achieve the predetermined relative guiding configuration.

9. The method of claim 1, wherein the guiding portion includes an arcuate guiding sleeve which substantially laterally surrounds at least a portion of the second elongate structure to achieve the predetermined relative guiding relationship.

10. The method of claim 1, wherein the step of laterally adjusting a transitory position of the first elongate structure includes the step of laterally adjusting the transitory position of the first elongate structure to substantially maintain at least one of the proximal second structure end and the second structure body in the predetermined guiding relationship with at least one fine-resolution guiding aid of the guiding portion of the guiding frame.

11. The method of claim 1, wherein the first elongate structure includes a penetration tool.

12. The method of claim 1, wherein the guiding frame has a plurality of laterally offset guiding structures, and including the step of selecting a chosen one of the laterally offset guiding structures to form the predetermined guiding relationship responsive to a desired lateral offset between the second elongate structure and the first elongate structure.

13. An apparatus for longitudinally guiding a first elongate structure for motion along a desired trajectory toward a target area through reference to a second elongate structure, the apparatus comprising:
   the first elongate structure, including longitudinally spaced proximal and distal first structure ends;
   the second elongate structure, including longitudinally spaced proximal and distal second structure ends separated by a second structure body, the second elongate structure being configured for placement in a predetermined targeting relationship with the target area, the predetermined targeting relationship being correlated with the desired motion trajectory, and the predetermined targeting relationship including the second elongate structure being located substantially lateral to the target area with the distal second structure end being located closer to the target area than is the proximal second structure end; and
   a guiding frame having a mounting portion and at least one laterally offset guiding structure, the guiding frame being configured for selective affixation to the first elongate structure in a predetermined relative guiding configuration; wherein
   at least one of the proximal second structure end and the second structure body is configured for placement into a predetermined guiding relationship with the guiding portion of the guiding frame; and the first elongate structure is configured for movement longitudinally toward the target area while a transitory position of the first elongate structure is laterally adjusted to maintain the at least one of the proximal second structure end and the second structure body in the predetermined guiding relationship with the guiding portion of the guiding frame.

14. The apparatus of claim 13, wherein the first elongate structure is moved longitudinally substantially along the desired motion trajectory with the assistance of the lateral adjustments made to maintain the at least one of the proximal second structure end and the second structure body in the predetermined guiding relationship with the guiding portion of the guiding frame.

15. The apparatus of claim 13, wherein the predetermined targeting relationship bears a predetermined direct correlation with the desired motion trajectory.

16. The apparatus of claim 13, wherein the distal second structure end is placed into contact with the target area during placement of the second elongate structure in the predetermined targeting relationship with the target area.

17. The apparatus of claim 13, wherein the proximal and distal first structure ends are longitudinally separated by a first structure body, and the guiding portion is located lateral to the first structure body such that the distal first structure end is located longitudinally closer to the target area than is the guiding portion while the first elongate structure is being moved longitudinally toward the target area.

18. The apparatus of claim 17, wherein the distal first structure end selectively penetrates the target area along the desired motion trajectory.

19. The apparatus of claim 13, wherein the mounting portion of the guiding frame includes a mounting collar that substantially laterally surrounds at least a portion of the first elongate structure to achieve the predetermined relative guiding configuration.

20. The apparatus of claim 13, wherein the mounting portion of the guiding frame is received by a mounting bracket of the first elongate structure to achieve the predetermined relative guiding configuration.

21. The apparatus of claim 13, wherein the guiding portion includes an arcuate guiding sleeve which substantially laterally surrounds at least a portion of the second elongate structure to achieve the predetermined relative guiding relationship.

22. The apparatus of claim 13, wherein the transitory position of the first elongate structure is laterally adjusted during longitudinal movement of the first elongate structure to substantially maintain at least one of the proximal second structure end and the second structure body in the predetermined guiding relationship with at least one fine-resolution guiding aid of the guiding portion of the guiding frame.

23. The apparatus of claim 13, wherein the first elongate structure includes a penetration tool.

24. The apparatus of claim 13, wherein the guiding frame has a plurality of laterally offset guiding structures, and a chosen one of the laterally offset guiding structures is selected to form the predetermined guiding relationship responsive to a desired lateral offset between the second elongate structure and the first elongate structure.

25. A guiding apparatus for longitudinally guiding at least a chosen one of a tool and a prosthetic component along a desired motion trajectory toward a target patient tissue through reference to a guide pin, the guiding apparatus comprising:

a guiding frame having a mounting portion and at least one laterally offset guiding structure, the guiding frame being configured for selective affixation to the chosen one of the tool and the prosthetic component in a predetermined relative guiding configuration; and the guiding portion being configured for placement into a predetermined guiding relationship with at least a portion of the guide pin; wherein the guide pin is configured for placement in a predetermined targeting relationship with the target patient tissue, the predetermined targeting relationship being correlated with the desired motion trajectory, and the guide pin being substantially located lateral to the target patient tissue; and wherein the chosen one of the tool and the prosthetic component, when in the predetermined relative guiding configuration with the guiding frame, being configured for movement longitudinally toward the target patient tissue while a transitory position of the chosen one of the tool and the prosthetic component is laterally adjusted to maintain the guide pin in the predetermined guiding relationship with the guiding portion of the guiding frame.

26. The guiding apparatus of claim 25, wherein the chosen one of the tool and the prosthetic component includes a proximal handle end and a distal tissue-contacting end, and the distal tissue contacting-end is located longitudinally closer to the target patient tissue than is the guiding portion of the guiding frame when in the predetermined guiding relationship with the chosen one of the tool and the prosthetic component.

27. The guiding apparatus of claim 25, wherein the mounting portion of the guiding frame includes a mounting collar that substantially laterally surrounds at least a portion of the chosen one of the tool and the prosthetic component to achieve the predetermined relative guiding configuration.

28. The guiding apparatus of claim 25, wherein the mounting portion of the guiding frame is received by a mounting bracket of the chosen one of the tool and the prosthetic component to achieve the predetermined relative guiding configuration.

29. The guiding apparatus of claim 25, wherein the chosen one of the tool and the prosthetic component includes a proximally-oriented handle end and a distally-oriented tissue-contacting end, and the mounting portion of the guiding frame is attached to the proximally-oriented handle end to achieve the predetermined relative guiding configuration with the guiding portion being located lateral to the distally-oriented tissue-contacting end.

30. The guiding apparatus of claim 29, wherein the guide pin is a first guide pin, a second guide pin is associated with the target patient tissue, and the distally-oriented tissue-contacting end includes a cannulated instrument for selective engagement with the second guide pin during movement of the chosen one of the tool and the prosthetic component, in the predetermined relative guiding configuration with the guiding frame, longitudinally toward the target patient tissue.

31. The guiding apparatus of claim 25, wherein the guiding frame has a plurality of laterally offset guiding structures, and a chosen one of the laterally offset guiding structures is selected to form the predetermined guiding relationship responsive to a desired lateral offset between the guide pin and the chosen one of the tool and the prosthetic component.

32. The guiding apparatus of claim 25, wherein the transitory position of the first elongate structure is laterally adjusted during longitudinal movement of the first elongate structure to substantially maintain at least one of the proximal second structure end and the second structure body in the predetermined guiding relationship with at least one fine-resolution guiding aid of the guiding portion of the guiding frame.

* * * * *